United States Patent [19]
Kotin et al.

[11] Patent Number: 5,580,703
[45] Date of Patent: Dec. 3, 1996

[54] HUMAN ADENO-ASSOCIATED VIRUS INTEGRATION SITE DNA AND USES THEREOF

[75] Inventors: Robert M. Kotin, Rockville, Md.; Kenneth I. Berns, Mamaroneck; Ralph M. Linden, New York, both of N.Y.

[73] Assignee: American Cyanamid Company, Wayne, N.J.

[21] Appl. No.: 308,949

[22] Filed: Sep. 20, 1994

Related U.S. Application Data

[63] Continuation of Ser. No. 947,127, Sep. 17, 1992, abandoned.
[51] Int. Cl.⁶ .......................... C12N 15/63; C12N 15/12; C12N 15/33
[52] U.S. Cl. .................. 435/320.1; 536/23.5; 536/23.72
[58] Field of Search ............................... 536/23.5, 23.72; 435/320.1, 235.1

[56] References Cited

PUBLICATIONS

Cohen, D., et al, (1993) Nature 366, 698–701.
Katin, R. M., et al. (1991) Genomies 10, 831–834.
Kotin, R. M., et al (1992) EMBO J. 11(13), 5071–5028.
Kotin, R. M., et al (1989) Virology 170, No. 460–467.
Kotin, R. M., et al., (1990) Proc. Natl. Acad. Sci., USA 87, 2211–2215.
Samulski, R. J., et al. (1991) EMBO J. 10(12), 3941–3950.
Das, H. K., et al. (1987) J. Biol. Chem. 262(10), 4787–4793.
Kotin, R. M. et al., "Mapping and Direct Visualization of a Region–Specific Viral DNA Integration Site on Chromosome 19q13—qter," EMBL Database entry Hssatvis; Accession No. M54997 (Jul. 23, 1991).
Berns, K. I., "Parvovirus Replication," *Microbiol. Rev.*, 54:316–329 (1990).
Samulski, F., et al., "Targeted integration of adeno–associated virus (AAV) into human chromosome 19," *EMBO J.*, 11:1228 (1992).

Primary Examiner—Charles L. Patterson, Jr.
Attorney, Agent, or Firm—Hamilton, Brook, Smith & Reynolds, P.C.

[57] ABSTRACT

The present invention relates to an isolated nucleic acid fragment comprising a nucleic acid sequence corresponding to a human AAV integration site, or a subsequence thereof which is site specific to the AAV integration site.

8 Claims, 10 Drawing Sheets

| | |
|---|---|
| 1 | GAATTCCTAACTGCCCCGGGGCAGTCTCTGCTATTCATCCCCTTTACGGGTGTGCTACACACACTTGCTAGTATGCCGTGGGG |
| 81 | ACCCCTCcggcCTGTAGACTCCATTCCCAGCATTCCCCGGAGGAGGCCCTCATCTGGCGATTCCACTGGGGCCTCGG |
| 161 | AGCTGCGGACTTCCCAGTGTGCATCGGGGCACAGCGACTCCTGAAGTGGCCACTTCTGCTAATGACTCCATTCCCAG |
| 241 | GCTCCCGCTACCTGCCAGCACACCCTGGGCATCCG<u>TGACGTCA</u>GCAAGCCG*GGGGCGGG*GACCGGAGATCCTTGGGGCGG |
| 321 | TGGGGGGCCAGCGGCAGTTCCCAGG*cggccCCCCGGGGGGCGGG*GTGGTGGGGCGGTTGGGGCGGTTGGGGCTCGGCGCT |
| 401 | CGCTCGCTCGCTGGG*CGGGCGGG*CGGTGCGATGTCCGGAGAGGAT*tgccg*CGCGGTCGGCCCGGGGGCGGCGCGGCTG |
| 481 | CCCGGAGCGGCGACGGGAGCAGCTGCGCGGCAGTCCTGGGCGCGGCCCGAGCCCTGGCCCCCGGAGAGCGCCGCGCCCG |
| 561 | CACCGTCCGCTTCGAGCGCGCCCGAGTTCCTGG*ggccTGTGCGGGGCGGCGCCCgcCGcgCCGGCCGTGACTCCACCAAC |
| 641 | GCGCCGCCGACCCTGCCCCCGGAGCTCGACCAGGCGCCGGCGTCTCCCGGGGGCGGCGTCTCCCGGGCCCAGGTCCACCCTCTGCCGCCACCT |
| 721 | GCCGACGGTATCAGCGCCCTGCACCAGGTCCAGTCTGCCAGTGTCCCCGTTGCCAGTCTCTCGATCCGGGTTCGTTACTGGCCTGGGTTTNCACCCTATGCTGACACCC |
| 801 | GGGGCATCCTCCTTCCCCCGTTGCCAGTCTCTCGATCCGGGTTCGTTACTGGCCTGGGTTTNCACCCTATGCTGACACCC |
| 881 | CGTTCCAGTCCCCCTTACCATTCCCCTTCGACCACCCCACTTCCGAATTCCGAGCGCTTCAACTGGCTGGGCTAGCACTCTGT |
| 961 | GTGACACTCTGAAGCTCTACATTCCCCTTCGACTCTCTTCGATTGGAGT<u>CGCTT</u>TAACTGGCCCTGGCTTTGGCAGC |
| 1041 | CTGTGCTGACCCATCGAGTCCTCCTTACCATCCCCTCCCTCGACTTCCCCTCTTCCGATGTTGAGCCCCTCCAGCCGGTCC |
| 1121 | TGGACTT<u>TGTCTCCTT</u>CCCTGCCCTCCTGAACCTGAGCCAGTCCCATAGCTCAGTTCTGGTCTATCTGCCTG |
| 1201 | GCCCTGGCCATTGTCACTTTGCGCTCTCTCTCCCTGCCCTTGCCCCGAGTGCCCTTGCTGTGCCGGAACTCTGCCCTCTAA |
| 1281 | CGCTGCCGTGCCGTCCGTTCTCTGAGTCCGGACCACTTTGAGCTCTCCCCTGGCTCTCTGCGCCTGGCCGCTTCTGTCTGCCCACTGTTTCC |
| 1361 | CCTTCCCAGGCAGGCTGCCGTCCTTGCCGCATTCTCTCCGCCGGTCCGCCTCCCGGCCGCCTTTCTGTCTGCAGCTTGTGGC |
| 1441 | CTGGGTCACCTTCTACGGCTGGCCCAAGATCCTTCCCTGCCGCCTCCTTCAGGTTCCGTCTTCCTCCACTCCCCTCTTCCCC |

Figure 1A

```
1521  TTGCTCTCTGCTGTGTTGCTGCCCAAGGATGCTCTTTCCGGAGCACTTCCTTCTCGGGGCTGCACCACGTGATGTCCTCT
1601  GAGCGGATCCTCCCGTGTCTGGGTCCTCTCCGGCATCTCTCACCCAACCCATGCCGTGTTCCGATGCCTTCACTCGCTGG
1681  GTTCCCTTTTCCTTCTCCTTCTCGGGCCTGTGCCATCTCTCGTTTCTTAGGATGCCTTCTCCGACGATGTCTCCCTTG
1761  CGTCCCGCCTCCCCTCTTGTAGCCTGCATCATCACCGTTTTTCTGGACAACCCAAAGTACCCCGTCTCCCTGGCTTA
1841  GCACCTCTCCATCCTCTTGCTTCTTGCCTGGACACCCCGTTCTCCTGTGGATTCGGGTCACCTCTCACTCCTTTCATT
1921  TGGGCAGCTCCCCTACCCCCCTTACCTCTCTAGTCTGTGCTAGCTCTTCCAGCCCCCTGTCATGGCATCTTCCAGGGTC
2001  CGAGAGCTCAGCTAGTCTCTTCTTCCTCCAACCCGGCCCTATGTCCACTTCAGGACAGCATGTTTGCTGCCTCCAGGATC
2081  CTGTGTCCCCGAGCTGGGACCACCTTATATTCCCAGGGCCGTTAATGTGGCTCTCTGGTTCTGGGTACTTTATCTGTCCC
2161  CTCCACCCCACAGTGGGGCCACTAGGGACAGAGATTGGTGACAGAAAAGCCCCCATCCTTAGCCTCCTCCTTCCTAGTCT
2241  CCTGATATTCGTCTAACCCCCACCTCCTGTTAGGCAGATTCCTTATCTGTGACACCCCCATTCCTGGAGCCATCTC
2321  TCTCCCTTGCCAGAACCTCTAAGGTTTGCTTACGATGGAGCCAGAGAGATCCTGGAGGAGACTTGGCAGGGGTGGGA
2401  GGGAAGGGGGGATGCGTGACCTGCCCGGTTCTCAGTGGCCGTTCTCCCAGAACCTGAGCTGCTCTGA
2481  CGCGGCTGTCTGGTGCTTTCACTGATCCTGGTGCTGCAGCTTCCTGGTTCTAACTTTGGCTCTTCACCTTTCTAGNCCCAATTTATATTGTTCCTCCGTG
2561  CAAAATCAGAATAAGTTGGTCTGAGAATGGTCGTCTAGGTGTTCACCAGTCGTGGCCGCTTCCGCCCCAGAGCAGGGTCGTGCCTTCCCTAAGGC
2641  CGTCAGTTTTACCTGTGAGATAAGGCCAGTAGCCACCCCGTGTTCACCAGTCGTGGCCGCTTCCGCCCCAGAGCAGGGTCGTGCCGTGTG
2721  GAAAACTCCCTTTGTAGAATGGTCGTCTAGGTGTTCACCAGTGCTATCTGGACATATTCCTCCGCCCCAGAGCAGGGTCGTGCCTTCCTCTTTCTCCAT
2801  CCATCCTTCTTCCTTAAAGAGCCTATCTGGACATATTCCTCCGCCCCAGAGCAGGGTCGTGCCTTCCCTAAGGC
2881  CCTGCTCTGGGCTTCTGGTTTGAGTCCTTGCAAGCCCAGTGCTAGCTTCCCTGTCCCCTTCCCTCGTCCACCAT
2961  CTCATGCCCTGCCTCTCCTGCCCTTCCTACAGGGTTCCTGCTCTGCTCTTCAGACTGAGCCCCGTTCCCCTGCATCC
```

Figure 1B

```
3041  CGGTTCCCCTGCATCCCCCTTCCCCTGCATCCCCCAGAGCCCCAGGCCACCTACTTGGCCTGAACCCCACGAGAGGCCA
3121  CCCAGCCCTGTCTACCAGGCTGACCTTTTGGGTGATTCTCCTCCAACTGTGGGTGACTGCTTGGGCAAACTCACTCTT
3201  CGGGGTATCCCAGGAGGCCTGGAGCATTGGGGTGGGGCTGGGGTTCAGAGAGGAGGATTCCCTCCAGGTTACGTGGCCAA
3281  GAAGCAGGGGAGCTGGGTTTGGGTCAGGCTGGGGTGTGGGGTGACCAGCTTATGCTGTTTGCCCAGGACAGCCTAGTTTTA
3361  GCGCTGAAACCCTCAGTCCTAGGAAAACAGGATGGTTGGTCACTGTCTCTGGGTGACTCTTGATTCCCGGCCAGTTTCT
3441  CCACCTGGGCTGTGTTTCTCGTCCTGCATCCTTCTCCAGCAGGTCCCCAAGCATCGCCCCCCATTCCTGCGCTGTTCCCAAGTT
3521  CTTAGGTACCCCACGTGGGTTTATGAACCACTTGGTGAGGCTGGTACCCTGCCCCCATTCCTGCACCCCAATTGCCTTAG
3601  TGGCTAGGGGGTTGGGGGCCTAGAGTAGGAGGGGCTGGGCCTGACTCCTGGGTCCGAGGAGGAGGGGCTGGGCCTGGACTCCTG
3681  GGCTCCTGGGTTTGAGAGAGGACTGGGGGCCTGGGGCCTGACTCCTGGGTCCGAGGAGGAGGGGCTGGGCCTGGACTCGTGGGTCTGA
3761  GGTCTGAGGGTGGAGGGACTGGGGGCCTGGGGCCTGACTTCTGGGTCTTAGGAGGCGGGACCCCTGGTTCTGAATGGGGAG
3841  GGGAGGAGGGTCGGGGGCCTGGACTTCTGGGTCTTAGGAGGCGGGACCCCTGGTTCTGAATGGGGAG
3921  AGGCTGGGGGCCTGGACTCCTTCATCTGAGGGCGAAGGGCTGGGCCCTGGCCCTCCTGGGTTGAATGGGGAGGGGGTTGGG
4001  CCTGGACTCTCGAGTCCCTGTGCCCAGGCCCTCAGGCCATCTTTCACAGGGATGCCTGTAC  4060
```

Figure 1C

▼ BamHI site

| recombination junction

```
                    1054            1034           1014          994
                      *               *              *            *
Cell  GGTAAGGAGGATCGATGGTCAGCACAGGCTGCCAAAGCCAGGGCCAGTTAAAGCGACTCCAATCGAAGAGAGTAGGTCG
               b'
AAV   TTGGCCACTCCCTCTCTGCGCGTCGCTCGCTCACTGAGGCCGCCCGGGCAAAGCCCGGGCTCGGGCGACCTTTGGTCGC
      *               *              *              *              *
      1              21             41             61
                    974             954
                     *               *
Cell  AAGGGAATGTAGAGCTTCAGAGTGTCACACAGAGTGCTAGCC
AAV   CCGGCCCTCAGTGAGCGAGCGAGCGCGCAGAGAGGGAGTGGCC
      *              *               *
      81            101             121

Figure 3B
```

```
Cell  ATCCCTCCCCTGACTTCCCCTCTTCCGATGTTGAGCCCCTCCAGCCGGTCCTGACTTTGTCTCTTCCCTGCCTTCCCTGCCCT
           *                    *                    *                    *
         1084                 1104                 1124                 1144
           |||||||||||||||||||||||||||||||||||||||||||||||| |||||||| ||||||||||||||
      TAATACAGGACCTCCCCTAACACTCAGTGACCCTAACCCTATGACGTAATTCACGTCACGACTCCTTCCCTGCCTTCCCTGCCCT
      TAATACAGGACCTCCCCTAACACTCAGTGACCCTAACCCTATGACGTAATTCACGTCACGACTCCACCCCCTCCAGGAACCC
AAV                              *                    *                    *
                               181                  161                  141

Cell  CTCCCTGAACCTGAGCCAGCTCCCATAGCTTCAGGTCTGGTCTGGTCTATCTGCCTGG
           *                    *                    *
         1164                 1184                 1101
           ||||||||||||||||||||||||||||||||||||||||||| |||||| | |||||
      CTCCCTGAACCTGAGCCAGCTCCCATAGCTTCAGGTCTGGTCTATCTGCCTGG
      CTAGTGATGGAGTTGGCCACTCCCCTCTTCTGCGCGCTCGCTCACTGAG
AAV       *                    *
        121                  101
```

Figure 3C

```
                     1184                      1164                      1144                      1124
                      *                         *                         *                         *
Cell ACCAGACCTGAGCTATGGGAGCTGGCTGAGGTTCAGGAGAGGGCAGGCAGGGAAGGAGACAAAGTCCAGGACCGGCTGGA
        |||||||||||||||||||||||||||||||||||||||||||||||||||||||||||||||||||||||||||||||
Cell GGGGAGCTGGGTTTGGGTCTGGGGTGTGGGGTGTGGGGCTGAGCTTATGCTGTTTTGCCCAGGACAAAGTCCAGGACCGGCTGGA
                                                         ↓
Cell GGGGAGCTGGGTTTGGGTCAGGCCTGGGGTGTGGGGTGTGGGGACCAGCTTATGCTGTTTTGCCCAGGACAGCCTAGTTTTAGCGCTGAA
      *                         *                         *                         *
     3293                      3313                      3333                      3353
                                e 1104                      1084
                      *                         *
Cell GGGGCTCAACATCGGAAGAGGGGAAGTCGAGGGAGGGAT
        |||||||||||||||||||||||||||||||||||||||
Cell GGGGCTCAACATCGGAAGAGGGGAAGTCGAGGGAGGGAT Cell ACCCTCAGTCCTAGGAAAACAGGGATGGTTGGTCACTCT
      *                         *
     3373                      3393 b'

Figure 3D
```

```
                    * *
                  A * *
                A A * *
              T A G C C C G G G C T
              T       | | | | X | | | |
              G A C G G G A C C G A C
                C                   A cellular - viral junction
              (1016-1013) X AAV nt(51-55)

T T G C C G G G C G
              T | | | | | | | | |
              T C G G C C C G C
                              A

AAV hairpin

Figure 3E

* * * *
                    T G T C T G G C
              T     | | | | X | | X |
              T C A G G T C C T G A
                                  G cell - cell junction
              (3346-3349)X(1131-1128)
```

5,580,703

HUMAN ADENO-ASSOCIATED VIRUS INTEGRATION SITE DNA AND USES THEREOF

GOVERNMENT SUPPORT

This work was supported by Grant No. AI 22251 from the United States Public Health Service. The United States Government has certain rights to this invention.

RELATED APPLICATION

This application is a continuation of application Ser. No. 07/947,127 filed on Sep. 17, 1992, now abandoned, which is incorporated herein by reference in its entirety.

Integration of vital DNA into eukaryotic cell DNA to establish latent infection occurs by non-homologous recombination. To date, adeno-associated virus (AAV) is unique among eukaryotic viruses in its ability to integrate site-specifically into the cellular genome (Kotin et al., 1990, 1991; Samulski et al., 1991, 1992). The targeting of the vital DNA constitutes a potential advantage for AAV derived vectors for human gene therapy. The vital DNA integrates into chromosome 19 (Kotin et al., 1990) at a site previously localized to position q 13.3 - q ter (Kotin et al., 1991, Samulski et al., 1991, 1992). This region of chromosome 19, which is well mapped both physically and genetically, is of interest for additional reasons. The locus for myotonic dystrophy (Asiandis et al., 1992) and a common breakpoint associated with chronic B-cell leukemia (BCL-3) (McKelthan et al., 1987; Korneluk et al., 1989) map to q 13.3. This region also experiences sister chromatid exchanges at high frequency (Fierchtinger & Schmid 1989).

Previous analyses of cellular genomic DNA indicated that there was no extensive similarity between viral and host sequences (Cheung et al., 1980; Laughlin et al., 1986; Kotin et al., 1990). This result was the basis for concluding that site-specific integration of vital DNA into the host genome occurs via non-homologous recombination. The specificity of the integration makes AAV an attractive model system for elucidating the Underlying mechanisms involved. Favorable features of an AAV based system are that the genetics and molecular biology of AAV have been well described (e.g., Berns, 1990). The relatively small vital genome (4.7 kb) has a simple genetic organization requiring a single vital open reading frame for gene expression, replication and possibly integration. Engineering AAV recombinants is facilitated because the cloned double-stranded vital DNA is infectious when transfected into cells. In addition, AAV is non-pathogenic in man and the initially latently infected cells of continuous lines did not display obvious deleterious phenotypic effects in vitro. However, as the assessment of phenotypic changes has become more sophisticated, it has become apparent that AAV latent infection does not affect phenotype as well as the expression of specific cellular genes (Bantel-Schaal and Stoehr, 1992; Walz and Schlehofer, 1992).

Currently, very little is known about the mechanism of non-homologous recombination. To proceed with the development of an AAV based vector for gene therapy, a better understanding of the processes involved in site-specific integration is essential. The original finding of site-specific integration was based on hybridization with cellular specific probes derived from sequences flanking the provirus in one clonal cell line (Kotin and Berns, 1989). These probes are used to analyze genomic DNA of other independently derived latently infected cell lines as well as uninfected cells (Kotin et al., 1990). Almost 70% of the analyzed latently infected cell lines display an additional restriction fragment that in about 50% of the cases also hybridizes to vital specific probes. These data indicate that a specific cellular sequence is disrupted by recombination with the vital DNA. Using in situ hybridization, the proviral DNA is co-localized to the pre-integration locus, AAVS1, in three independently derived cell lines, providing further evidence that the pre-integration site is associated with viral sequences (Kotin et al., 1991). These results are supported by a recent report analyzing the integration sites of other cell lines (Samulski et al., 1991 and 1992) also using the flanking cellular sequences as probes.

To characterize the mechanism of non-homologous recombination, a comparison of the pre-integration sequence to the provital junction sequences is necessary. Analysis of the cellular sequence may indicate which signals contribute to the specificity of the recombination event. To this end, the present invention provides a cloned, sequenced 4 kb sub-fragment of AAVS1, including the AAV DNA integration site. Sequence analysis also reveals within this fragment a putative TATA-less promoter with a cyclic AMP response element. Consistent with the presence of a promoter, the locus is found to be transcribed in fibroblasts and endothelial cells.

SUMMARY OF THE INVENTION

The present invention provides an essentially pure nucleic acid fragment containing a sequence corresponding to a human adenoassociated virus (AAV) integration site, or portions thereof which are specific to the integration site sequence. In accordance with the proposed use of AAV as a vector for gene therapy, the nucleic acid sequence encoding the integration site can be employed as a probe, in conjunction with gene therapy, to identify successful integration of AAV into a specific chromosome 19 locus. Moreover, the RAY integration site-specific portions can be used as primers in PCR-based detection of targeted integration.

Also provided by the present invention is a novel structural gene encompassed within the 4 kb fragment comprising the RAY integration site. The gene is characterized by the presence of a TATA-less promoter and a cyclic AMP responsive element.

BRIEF DESCRIPTION OF THE FIGURES

FIGS. 3A–3C. The recombination junctions are shown in FIGS. 3A–3C. FIG. 3A shows a graphical scheme of the preinsertion site (AAVS1). Letters indicate AAVS1 DNA sequences involved in the recombination process and refer to random locations on the AAVS1 DNA sequence, where "b", for example, represents one region of the AAVS1 DNA sequence involved in the recombination process. Numbers designate the recombination junctions. FIG. 3B depicts alignments of the sequences at the recombination junctions. The letters correspond to FIG. 3A (SEQ ID NOS: 2 to 10). Underlined regions display sequence homologies between the recombination partners at the junctions. The vertical arrows highlight AAVS1 nucleotides involved in 2 recombination events. "Cell" designates AAVS1 sequences from uninfected cells and "AAV" designates wildtype AAV sequences. The middle sequence corresponds to the nucleotide sequences at the recombination junctions of DNA obtained from cells infected with AAV. The letter "b'" refers to the reverse complement of the AAVS1 DNA sequence designated "b" in FIG. 3A. Three different sets of sequences are provided with each sequence set corresponding to the recombination junction (1, 2 or 3) at which a recombination event occurs. FIG. 3C is a comparison of possible secondary structures at the recombination sites to the AAV hairpin of the terminal repeats. The nucleotide numbers given correspond to FIG. 3B and are referred to in the Examples. Asterisks indicate regions of homologies referred to in FIG. 3B (SEQ ID NOS: 11 to 13). Three possible secondary structures at the recombination sites to the AAV hairpin are shown. The nucleotide numbers correspond to the underlined sequences shown in FIG. 3B (shown in reverse complement). The asterisk represents sequences of exact identity and the "x" represents the location of the recombination event.

FIG. 4. Amplification of the cDNA derived from reverse transcription by polymerase chain reaction (PCR). The reactions are carried out as described in the Examples. M: molecular weight marker; 5', 3', 5'+3': indicate specific primers (RK1, RK2, RK1+RK2) used for the reverse transcription reaction. PCR is carried out in the presence of both RK1 and RK2.

DETAILED DESCRIPTION OF THE INVENTION

Figure 1D:
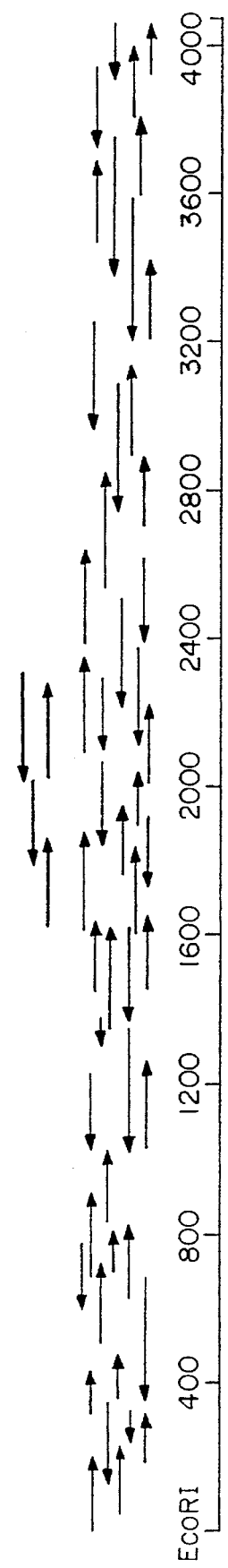
FIGS. 1 through 1A show the sequence of the AAV integration locus, AAVS1 (SEQ ID NO: 1). The transcription factor binding elements are indicated: lowercase for upstream binding factor (UBF1), italicized for SP1. The octamer for the cAMP response element (CRE) is indicated by a box. Underlined bold typed sequences represent short stretches of homology between donor and acceptor at the observed recombinational junctions. The region corresponding to a partial cDNA is underlined. Arrows indicate chromosome 19 specific minisatellite sequences.
FIG. 1B is a schematic diagram depicting the strategy followed to determine the AAVS1 sequence. Bold typed arrows indicate the sequencing strategy applied for a partial cDNA clone.

To isolate the AASV1 integration site, a human embryonic lung fibroblast λ phage library is screened using flanking probes earlier described (Kotin and Berns, 1989). A 12 kb insert is identified in a clone which hybridizes to both probes. From this insert, an approximately 8 kb EcoRI fragment is subcloned and partially sequenced. A 4,060 bp region is focused on within this 8 kb fragment (FIG. 1B). This 4 kb region contains at least two major features: (1) the recombinant junctions indicating the site of AAV integration and (2) a novel promoter and gene sequence. The integration site is characterized by the recombination junctions ± approximately 1 kb on either side of the junctions (FIGS. 1 through 1A).

The novel promoter/gene is characterized by a region of high G+C concentration in nucleotides 1–900, indicating the presence of a CpG island. CpG have been previously identified in the literature as being associated with the 5' ends of genes and TATA-less promoters. In fact, this region of the AAVS1 sequence lacks a TATA-like element. Other landmarks within the CpG island are SP1-like binding sites, at nucleotides 292–299, 358–373 and 416–423, a cAMP response element at 278–285, and nine upstream binding factor 1 sequences (CGGCC or GGCCG). Although the identity of the protein encoded by this gene is not certain, the presence of these elements indicate it is a regulated protein, and that the gene is thus not just a constitutive housekeeping gene.

To further corroborate this assumption, attempts are made to identify an mRNA corresponding to sequences downstream from the putative promoter. Initial attempts to identify such transcripts by Northern analysis of various cell lines using flanking sequences as probes are unsuccessful. However, use of oligos corresponding to nucleotides 1586–1605 and the reverse complement of nucleotides 1889–1906 as primers for production of cDNA and subsequent PCR analysis yield a product of approximately 330 bp (FIG. 4). Since priming only with the upstream oligo does not result in a PCR product, it can be concluded that the signal is derived from an mRNA molecule, and not from plasmid or contaminating genomic DNA. The PCR product is further used to screen fibroblast cDNA library. A positive plaque is isolated and the insert cloned and sequenced. The cDNA isolated in this manner corresponds to nucleotides 1609–2308 in the genomic sequence. The longest open reading frame within the cDNA sequence is 95 residues and a 3' untranslated region, with no polyadenylation site. The cDNA or corresponding genomic DNA, can be used as probes for further library screening for the full length gene. This evidence further confirms that AAVS1 is transcriptionally active.

Each of the positions of the sequence described above provide useful research tools in the study of the processes involved in nonhomologous recombination. For example, the presence of a potential promoter as well as indicator of transcriptional activity of the preinsertion site may lead to an additional targeting cue. In the case of adenovirus integration, for example, mammalian targeting sequences have been shown to be transcriptionally active and the altered chromatin structures were thought to have enhancing effects on the frequency of recombination (Lichtenberg et al., 1987, Schulz et al., 1987). The sequence elements defined above, found within a 4 kb range, are believed to be sufficient to define a unique genomic nucleus that has potential for forming stable structural features.

In another embodiment, the 4 kb nucleic acid sequence, or portions thereof, can be employed as an adjunct to the use of AAV as a vector in gene therapy. An AAV-based system for targeted integration of exogenous DNA into the cellular genome has certain potential advantages over other methods, e.g. retrovital vectors, for gene therapy. The defined site of integration of AAV would likely be preferable to the essentially random integration seen with retrovital DNA. The effects on the cell of disrupting a defined locus and how this genomic environment may effect expression of a transgene can be determined empirically, whereas the consequences of random integration are unpredictable and potentially disruptive to normal cellular function. Also, to date, AAV has not been shown to be the causative agent of any diseases in humans, unlike retroviruses.

The nucleic acid sequences, either all or any portion of the 4 kb fragment or the cDNA derived therefrom, are useful as probes in identifying successful integration of an AAV vector delivering an exogenous gene of interest. Methods for such use of the probes in question are disclosed in, for example, Kotin and Berns (1989), the contents which are incorporated herein by reference. The sequences may also be used as probes for identifying disruptions in this region of the chromosome that may be associated with disease states such as acute myelogenous leukemia.

EXAMPLES

Cloning of AAVS1

The λ EMBL library produced from human embryonic lung fibroblast DNA, W138 (Stratagene) is hybridized to both "right" and "left" flanking probe as previously described (Kotin and Berns, 1989). Two overlapping recombinant phages are isolated as positive clones: the first hybridizes to the left flanking probe exclusively and contains approximately 18 kb, the second clone hybridizes to both left and right flanking probes and contains an approximately 12 kb insert. An 8.2 kb EcoRI fragment positive to the left and right flanking probe is subcloned into pBluescript (Stratagene). This pRI-A fragment is further subcloned for DNA sequencing (see below).

Subclones for sequencing are produced either by a shotgun approach using Ava1 or Sau3a or by specifically cloning discrete subfragments generated by digestion with various restriction endonucleases, e.g., PstI or SmaI. Nested deletions are produced by limited digestion with exonuclease III (Pharmacia) as described by the manufacturer. The DNA sequence is determined by the dideoxynucleotide termination method (Sanger et al., 1980) adapted for double-stranded DNA (US Biochemicals, Sequenase kit, 2.0). Single-stranded templates and deaza-dGTP are utilized if required. Sequences highly enriched in G+C are confirmed by repeated sequencing using the dsDNA Cycle Sequencing System (BRL) or the Bst Sequencing Kit (BioRad). As primers the commercially available Reverse-, T3-, T7-, KS-, SK-primer (Stratagene) are used as recommended. In addition, AAVS1 specific primers are obtained from oligos and used without further purification:

RML1: 5'CTTTGGCAGCCTGTGCTGA-3' (SEQ ID NO: 14);

RML2: 5'CTGGACGAGGCGCGTCTGATG-3' (SEQ ID NO: 15);

RML5: 5'AGCGCAAAGTGACAATGGCCA-3' (SEQ ID NO: 16;

RK1: 5'GAGAGGTGACCCGAATCCAC-3' (SEQ ID NO: 17);

RK2: 5'CACGTGATGTCCTCTGAGCG-3' (SEQ ID NO: 18);

RK3: 5'GTTGCCAGTCTCGATCCGCCCC-3' (SEQ ID NO: 19);

KL1: 5'GGGCTGTGGTGAGGAGGGG-3' (SEQ ID NO: 20);

KL2: 5'AGCGCTAGCTTCCCTGTCCC-3' (SEQ ID NO: 21);

KL3: 5'ACTGTTCGGGGTATCCCAG-3' (SEQ ID NO: 22);

KL4: 5'TCCTGCATCCTTCTCCAGGC-3' (SEQ ID NO: 23).

Computer analysis of nucleotide and deduced amino acid sequences are performed using software from the Genetics Computer Group Inc. (version 7-unix, Devereauz et al., 1984) and IntelliGenetics Inc. (release 5.4).

The DNA sequence of 4,560 bp (FIGS. 1 through 1A) from the 8.2 kb fragment is determined. This 4 kb fragment contains the AAV integration site.

Figure 2A:
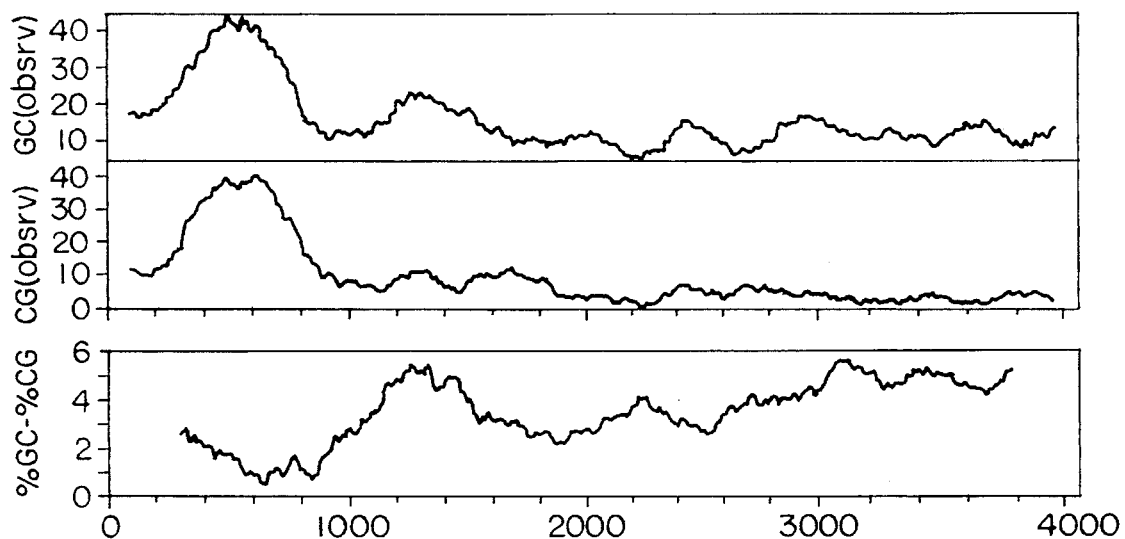
FIG. 2A depicts the relative frequencies of the dinucleotides of GC and CG within the sequence of FIGS. 1 through 1A are shown. The table of these frequencies was obtained using the GCG program Window with a window size of 200 and a shift increment of 6.

Overall, the sequence is 65% G+C with a particularly high G+C concentration from nucleotides 1–900 where the content is 82% G+C. It is this region which matches the requirements for CpG islands (Bird, 1987) in the overall % G+C and the length of the >60% G+C sequence. Furthermore, throughout the sequence determined it is only this region which shows an approximately equal distribution of CpG relative to GpC (FIG. 2A). CpG islands have been associated with the 5'-ends of genes and with some TATA-less promoters. Within this CpG island are three tandems of Sp1-like binding sites located at nucleotides 292–299; 358–373 and 416–423 (FIGS. 1 through 1A). No typical TATA or TATA-like element is found in this region of the sequence. The sequence for the cyclic AMP (cAMP) responsive element (CRE), TGACGTCA (Montminy et al., 1986), is between nucleotides 278–285 within the CpG island. This octamer has been shown to interact with the leucine zipper class of transcription factors known as CREBs (for cAMP response element binding proteins) (rev. by Habener, 1990). The sequence for the upstream binding factor 1 (UBF1) CGGCC or the reverse complement, GGCCG (Bell et al., 1988) is located at nine positions within the CpG island at nucleotides: 88, 346, 446, 596, 682 and 693. Three additional UBF1 sequences are distributed through the rest of the sequence at positions 2117, 2770 and 3429 (FIG. 1B).

Search for possible coding regions reveals several open reading frames (orf) throughout the sequence characterized. Comparison of all possible deduced peptides to the available databases results in no significant homologies indicating a novel gene product derived from the transcriptional activity described below. Furthermore, it is notable that no perfect polyadenylation signal is found throughout the sequence presented.

Figure 2B:
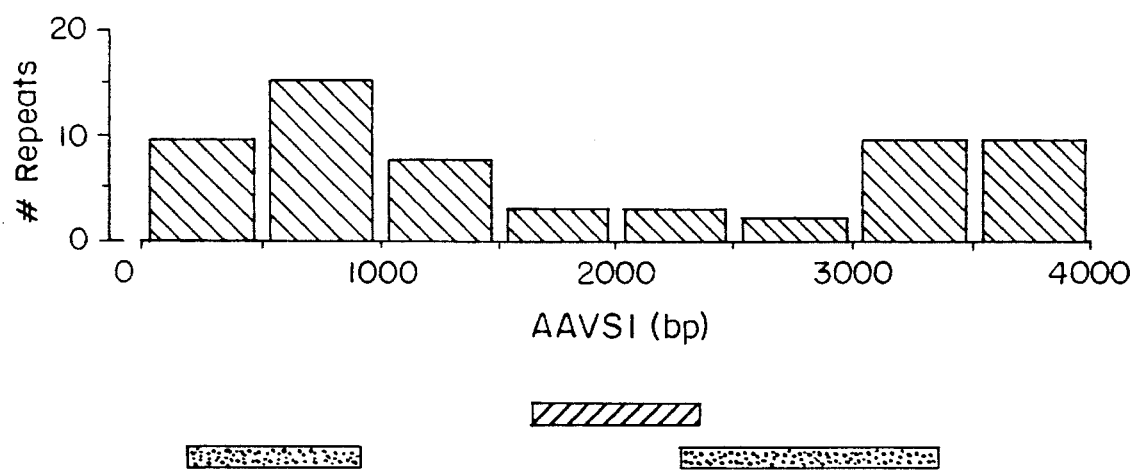
FIG. 2B depicts the frequency of repeat units occurring throughout AAVS1. The analysis was performed using the Repeat program of the GCG suite with a window size of 13 and a stringency of 12. As a control the same parameters were applied for the analysis of AAVS1 randomized by the GCG program Shuffle resulting in a frequency of 3 repeat units/1000 bp (data not shown). The hatched box shows the position of the cDNA isolated from a lambda cDNA library. The grey boxes indicate the positions of putative protein-coding regions predicted by a coding recognition module (CRM) designed to provide an indication of the coding potential of a sequence (Uberbacher and Mural, 1991).

Additional analysis of AAVS1 yields a large number of repetitive elements occurring at higher than random frequencies. Because of the high G+C, only direct repeats of 11 nucleotides or longer are scored (FIG. 2B). Twenty-one distinct direct repeats are found throughout the 4 kb sequence. Within the region containing the CpG Island (nucleotides 1–1500) the repeats are evenly distributed, averaging one repeated sequence motif approximately every 45 bp. Throughout the following 1300 bp (nucleotides 1501–2800), only six repeat motifs are found giving an average of 1 every 220 bp. Within the next 800 bp (nucleotides 2801–3600) 11 repetitive sequence motifs are found at an average distribution of 1 every 70 bp. The chromosome 19 q specific mini-satellite sequence previously described (Das et al., 1987) is at nucleotide 3648–4015 with an array of ten basic repeat units (Kotin et al., 1991). The middle third of the AAVS1 sequence which has the lowest density of repeats is also the region where several extensive open reading frames are located (FIG. 2B).

Database (Genbank; EMBL) searches indicate that AAVS1 is a novel sequence. To address whether sequence motifs previously reported as being associated with recombination are present at or near the sites of AAV integration and associated rearrangements, comparison using 100 nucleotide subfragments of AAVS1 as probes to available databases are made. The only sequences exceeding 70% homology (>10 standard deviations above mean) to an AAVS1 probe sequence is within the short terminal repeat region of herpes simplex virus I (HE1CG GenBank).

Transcription from AAVS1

The sequencing results indicate that a putative promoter is located within the CpG island. If this is the case, then a transcript complementary to downstream sequences which contain an open reading frame will be predicted. Initial attempts to detect such a transcript by northern analysis of RNA from HeLa and KB cell lines are negative when the right or left flanking sequences are used as probes. Oligonucleotides corresponding to nucleotides 1586–1605 and the reverse complement of nucleotides 1889–1908 are used as primers for the production of cDNA and subsequent analysis by PCR. Total RNA from embryonic human foreskin fibroblasts is isolated by the RNAxol Method (Biotex Laboratories, Inc., Tex.) following the procedure recommended by the manufacturer. 2 µg of the RNA and 0.2 µg of the specific primers (RK1 and/or RK2) are heated for 1 minute to 90° C. and then rapidly cooled on ice. The volume is adjusted 96 µl with $H_2O$, PCR buffer (final concentration: 10 mM Tris-HCl, pH 8.4, 50 mM KCl, 1.5 mM $MgCl_2$, 0.01% gelatine) and the four deoxynucleotides triphosphates at 0.25 mM. Reverse transcription is started by addition of 40 U of RNasin (Boehringer) and 20 U of Murine Moloney leukemia virus reverse transcriptase. The reaction is carried out at room temperature for 10 minutes and continued at 37° C. for 60 minutes. Finally the products are heated to 95° C. for 5 minutes and stored at −20° C. Amplification of the cDNA by PCR is carried out according to standard protocols recommended by the manufacturer (Perkin Elmer Cetus, Norwalk, Conn.). After 40 cycles at 94° C. for denaturing (1 minute), 55° C. for annealing (2 minutes), and 72° C. for synthesis (2 minutes) 10% of the resulting product mixtures are analyzed by gel electrophoresis on a 1.3% agarose gel.

A PCR product of approximately 330 bp is generated only when the downstream oligo is used to prime the reverse transcriptase reaction (FIG. 4). Priming with only the upstream oligo does not result in a PCR product which indicates that the signal is derived from an RNA molecule and not from contaminating plasmid or genomic DNA. Therefore the sense strand is as written in FIGS. 1 through 1A.

To add further evidence to the finding that AAVS1 is transcriptionally active, the PCR product is used to screen a λ library of fibroblast cDNA. A λ cDNA library produced from human fibroblast RNA (W138, Stratagene) is hybridized to the RT-PCR product described above. One recombinant phage is isolated as positive clone. A 700 bp insert is subcloned into pBluescript and the sequence is determined according to the strategy shown in FIG. 1B. The cDNA corresponds to the genomic sequence from nucleotides 1609 to 2308. This sequence consists of an open reading frame of 95 residues and 3' untranslated sequence as evidenced by the multiple termination codons in each reading frame. As also described for the genomic DNA, no polyadenylation site is found within the cDNA clone.

DNA Rearrangements Associated with Viral DNA Integration

Figure 3A:
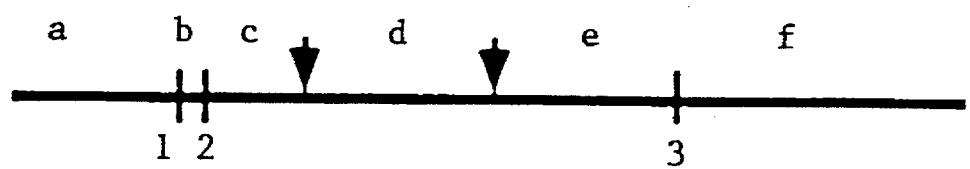

Rearrangements of the cellular DNA occurs as a result of viral DNA integration as determined by comparing the sequence of the provital junctions in the one cell line previously characterized (Kotin and Berns, 1989) with the homologous sequence from uninfected cells. These recombinational events are shown in FIG. 3A. The vital-cellular junction, referred to as the right flank junction (Kotin and Berns, 1989), corresponds to the cellular sequence from the BamHI site at 1620 to nucleotides (1144–1147) X AAV nucleotides (154–157), where X designates a site of recombination. At the site of recombination there are 4 nucleotides, GGAG (or the reverse complement), common to both the viral and cellular sequences (FIG. 3B). The "left" junction (Kotin and Berns, 1989) is generated by at least two recombinational events: one involving only cellular sequences and another between vital and cellular sequences. The latter recombination involves nucleotides 1012–1016 of the cellular sequence and nucleotides 51–55 of the flop conformer of the RAY terminal repeat. Five nucleotides (GCTTT or the reverse complement), at the site of a recombination, are common to both the viral and cellular DNAs. The recombinational event involving only cellular sequences occurs between positions separated by 2 kb: nucleotides 1128 and 3346. At this site there are four nucleotides common to both strands (GACA or the reverse complement). Therefore, the "left" junction has the following organization (referenced to the sequence in FIG. 1A). BamHI site at nucleotides 2369–(3346–3349) X (1131–1128)–(1016–1013) X AAV nucleotides (51–55). As a consequence of the recombination and inversion involving only the cellular sequences, a structure resembling one cross-arm of the AAV tr (terminal repeats) is generated (FIG. 3C). Furthermore, this hairpin contains a direct repeat of 7 nucleotides. It is interesting to note that between nucleotides 1128 and 1134 two recombinational events occur with the central nucleotide #1131 involved in both events. This result suggests that both recombinational events, i.e., cellular-cellular and viral-cellular, occur coordinately. These recombinations present a topological problem requiring a complex model to account for the data.

Sequences consisting of five or more As (adenosines) and/or Ts (thymidines) have been described as preferred sites for non-homologous recombination in mammalian cells (Konopka, 1988). The five nucleotide sequence, TTTAA, is found at the recombination site at nucleotide 1028–1020. The sequence TTTTA is located at nucleotides 3356–3360 within 10 nucleotides of the recombination point at 3346–3349. However no A+T rich stretch is found at or near nucleotides 1128–1134; the site involved in two recombination events.

The involvement of topoisomerase I (Topo I) in nonhomologous recombination has been previously described (rev. by Champoux et al., 1988). A highly preferred Topo I cleavage site, CTT (Konopka, 1988) is on both substrates at the viral cellular junction, at 1015–1017 and nucleotides 54–51 (as the reverse complement). The Topo I cleavage site CTC is present at: the viral-cellular junction involving nucleotides 1131–1133 and AAV nucleotides 157–155; and at the junction between cellular sequence 3344–3346 and 1131–1133.

DEPOSIT OF BIOLOGICAL MATERIALS

The following biological materials have been deposited with the American Type Culture Collection, 12301 Parklawn Drive, Rockville, Md. 20852, under the Budapest Treaty, and given the indicated Accession Numbers:

| Description | Accession No. |
| --- | --- |
| E. coli DH5α containing plasmid pRIA-N3 | ATCC 69065 |

What we claim is:

1. An essentially pure nucleic acid having the sequence in SEQ ID NO: 1.

2. The nucleic acid of claim 1 which is about 4 kb.

3. An essentially pure nucleic acid having nucleotides 1609–2308 in SEQ ID NO: 1.

4. An essentially pure nucleic acid having the following characteristics:
  (a) a TATA-less promoter located at nucleotide positions 1–900 in SEQ ID NO: 1 comprising three SP1-like binding sites, a cyclic AMP responsive element and at least six upstream binding factor 1 sequences, wherein:
    (i) the SP1-like binding sites are located at nucleotides 292–299, 358–373 and 416–423 in SEQ ID NO: 1;
    (ii) the cyclic AMP responsive element has the nucleotide sequence TGACGTCA and is located at nucleotides 278–285 in SEQ ID NO: 1;
    (iii) the six upstream binding factor 1 sequences have the sequence CGGCC or the reverse complement GGCCG and are located at nucleotide positions 88, 346, 446, 596, 682 and 683 in SEQ ID NO: 1;
  (b) a gene that is transcriptionally active located at nucleotides 1609–2308 in SEQ ID NO: 1;
  (c) three recombination event sites located at nucleotides 1013–1016, 1128–1134 and 3346–3349;
  (d) at least three additional upstream binding factor 1 sequences located at nucleotide positions 2117, 2770 and 3429; and
  (e) is isolatable from chromosome 19.

5. A recombinant vector comprising the nucleic acid of claim 1.

6. A recombinant vector comprising the nucleic acid of claim 4.

7. A primer for use in detection of adeno-associated virus integration comprising an essentially pure nucleic acid having the sequence in SEQ ID NO: 1.

8. A primer selected from the group consisting of: SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22 and SEQ ID NO: 23.

* * * * *

UNITED STATES PATENT AND TRADEMARK OFFICE
CERTIFICATE OF CORRECTION

PATENT NO. : 5,580,703
DATED : December 3, 1996
INVENTOR(S) : Robert M. Kotin, Kenneth I. Berns and Ralph M. Linden It is certified that error appears in the above-indentified patent and that said Letters Patent is hereby corrected as shown below:

On the cover page, after "Assignee: American Cyanamid Company, Wayne, N.J.", insert -- and Cornell Research Foundation, Inc., Ithaca, N.Y. --.

Signed and Sealed this

Twenty-second Day of July, 1997

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 4060 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
GAATTCCTAA  CTGCCCCGGG  GCAGTCTGCT  ATTCATCCCC  TTTACGCGGT  GCTACACACA       60
CTTGCTAGTA  TGCCGTGGGG  ACCCCTCCGG  CCTGTAGACT  CCATTTCCCA  GCATTCCCCG      120
GAGGAGGCCC  TCATCTGGCG  ATTTCCACTG  GGGGCCTCGG  AGCTGCGGAC  TTCCCAGTGT      180
GCATCGGGGC  ACAGCGACTC  CTGGAAGTGG  CCACTTCTGC  TAATGGACTC  CATTTCCCAG      240
GCTCCCGCTA  CCTGCCCAGC  ACACCCTGGG  GCATCCGTGA  CGTCAGCAAG  CCGGGCGGGG      300
ACCGGAGATC  CTTGGGGCGG  TGGGGGGCCA  GCGGCAGTTC  CCAGGCGGCC  CCCGGGGCGG      360
GCGGGCGGGC  GGGTGGTGGC  GGCGGTTGGG  GCTCGGCGCT  CGCTCGCTCG  CTGGGCGGGC      420
GGGCGGTGCG  ATGTCCGGAG  AGGATGGCCG  GCGGCTGGCC  CGGGGCGGC   GGCGCGGCTG      480
CCCGGGAGCG  GCGACGGGAG  CAGCTGCGGC  AGTGGGGCGC  GGGCGGGCGC  CGAGCCTGGC      540
CCCGGAGAGC  GCCGCGCCCG  CACCGTCCGC  TTCGAGCGCG  CCGCCGAGTT  CCTGGCGGCC      600
TGTGCGGGCG  GCGACCTGGA  CGAGGCGCGT  CTGATGCTGC  GCGCCGCCGA  CCCTGGCCCC      660
GGCGCCGGAG  CTCGACCCCG  CCGGCCGCCG  CCCGCCCGCG  CCGTGCTGGA  CTCCACCAAC      720
GCCGACGGTA  TCAGCGCCCT  GCACCAGGTC  AGCGCCCCCC  GCGGCGTCTC  CCGGGGCCAG      780
GTCCACCCTC  TGCGCCACCT  GGGGCATCCT  CCTTCCCCGT  TGCCAGTCTC  GATCCGCCCC      840
GTCGTTACTG  GCCCTGGGTT  TNCACCCTAT  GCTGACACCC  CGTTCCAGTC  CCCTTACCAT      900
TCCCTTCGAC  CACCCCACTT  CCGAATTGGA  GCGCTTCAAC  TGGCTGGGCT  AGCACTCTGT      960
GTGACACTCT  GAAGCTCTAC  ATTCCCTTCG  ACCTACTCTC  TTCGATTGGA  GTCGCTTTAA     1020
CTGGCCCTGG  CTTTGGCAGC  CTGTGCTGAC  CCATCGAGTC  CTCCTTACCA  TCCCTCCCTC     1080
GACTTCCCCT  CTTCCGATGT  TGAGCCCCTC  CAGCCGGTCC  TGGACTTTGT  CTCCTTCCCT     1140
GCCCTGCCCT  CTCCTGAACC  TGAGCCAGCT  CCCATAGCTC  AGGTCTGGTC  TATCTGCCTG     1200
GCCCTGGCCA  TTGTCACTTT  GCGCTGCCCT  CCTCTCGCCC  CGAGTGCCC   TTGCTGTGCC     1260
GCCGGAACTC  TGCCCTCTAA  CGCTGCCGTG  CCGTCTCTCT  CCTGAGTCCG  GACCACTTTG     1320
AGCTCTACTG  GCTTCTGCGC  GCCTCTGGCC  CACTGTTTCC  CCTTCCCAGG  CAGGTCCTGC     1380
TTTCTCTGAC  CAGCATTCTC  TCCCCTGGGC  CTGTGCCGCT  TTCTGTCTGC  AGCTTGTGGC     1440
CTGGGTCACC  TCTACGGCTG  GCCCAAGATC  CTTCCCTGCC  GCCTCCTTCA  GGTTCCGTCT     1500
TCCTCCACTC  CCTCTTCCCC  TTGCTCTCTG  CTGTGTTGCT  GCCCAAGGAT  GCTCTTTCCG     1560
GAGCACTTCC  TTCTCGGCGC  TGCACCACGT  GATGTCCTCT  GAGCGGATCC  TCCCCGTGTC     1620
TGGGTCCTCT  CCGGGCATCT  CTCCTCCCTC  ACCCAACCCC  ATGCCGTGTT  CACTCGCTGG     1680
GTTCCCTTTT  CCTTCTCCTT  CTGGGCCTG   TGCCATCTCT  CGTTCTTAG   GATGGCCTTC     1740
TCCGACGGAT  GTCTCCCTTG  CGTCCCGCCT  CCCCTTCTTG  TAGGCCTGCA  TCATCACCGT     1800
```

```
TTTTCTGGAC AACCCCAAAG TACCCCGTCT CCCTGGCTTA GCACCTCTCC ATCCTCTTGC   1860
TTTCTTTGCC TGGACACCCC GTTCTCCTGT GGATTCGGGT CACCTCTCAC TCCTTTCATT   1920
TGGGCAGCTC CCCTACCCCC CTTACCTCTC TAGTCTGTGC TAGCTCTTCC AGCCCCTGT    1980
CATGGCATCT TCCAGGGGTC CGAGAGCTCA GCTAGTCTTC TTCCTCCAAC CCGGGCCCTA   2040
TGTCCACTTC AGGACAGCAT GTTTGCTGCC TCCAGGGATC CTGTGTCCCC GAGCTGGGAC   2100
CACCTTATAT TCCCAGGGCC GGTTAATGTG GCTCTGGTTC TGGGTACTTT TATCTGTCCC   2160
CTCCACCCCA CAGTGGGGCC ACTAGGGACA GGATTGGTGA CAGAAAAGCC CCCATCCTTA   2220
GGCCTCCTCC TTCCTAGTCT CCTGATATTC GTCTAACCCC CACCTCCTGT TAGGCAGATT   2280
CCTTATCTGG TGACACACCC CCATTTCCTG GAGCCATCTC TCTCCTTGCC AGAACCTCTA   2340
AGGTTTGCTT ACGATGGAGC CAGAGAGGAT CCTGGGAGGG AGACTTGGCA GGGGGTGGGA   2400
GGGAAGGGGG GGATGCGTGA CCTGCCCGGT TCTCAGTGGC CACCCTGCGC TACCCTCTCC   2460
CAGAACCTGA GCTGCTCTGA CGCGGCTGTC TGGTGCGTTT CACTGATCCT GGTGCTGCAG   2520
CTTCCTTACA CTTCCCAAGA GGAGAAGCAG TTTGGAAAAA CAAAATCAGA ATAAGTTGGT   2580
CCTGAGTTCT AACTTTGGCT CTTCACCTTT CTAGNCCCCA ATTTATATTG TTCCTCCGTG   2640
CGTCAGTTTT ACCTGTGAGA TAAGGCCAGT AGCCACCCCC GTCCTGGCAG GGCTGTGGTG   2700
AGGAGGGGGG TGTCCGTGTG GAAAACTCCC TTTGTGAGAA TGGTGCGTCC TAGGTGTTCA   2760
CCAGGTCGTG GCCGCCTCTA CTCCCTTTCT CTTTCTCCAT CCATCCTTCT TTCCTTAAAG   2820
AGCCCCCAGT GCTATCTGGA CATATTCCTC CGCCCAGAGC AGGGTCCGCT TCCCTAAGGC   2880
CCTGCTCTGG GCTTCTGGGT TTGAGTCCTT GCAAGCCCAG GAGAGCGCTA GCTTCCCTGT   2940
CCCCCTTCCT CGTCCACCAT CTCATGCCCT GGCTCTCCTG CCCCTTCCTA CAGGGGTTCC   3000
TGGCTCTGCT CTTCAGACTG AGCCCCGTTC CCCTGCATCC CCGTTCCCCT GCATCCCCCT   3060
TCCCTGCAT CCCCCAGAGC CCCAGGCCAC CTACTTGGCC TGGAACCCCA CGAGAGGCCA    3120
CCCCAGCCCT GTCTACCAGG CTGACCTTTT GGGTGATTCT CCTCCAACTG TGGGGTGACT   3180
GCTTGGGCAA ACTCACTCTT CGGGGTATCC CAGGAGGCCT GGAGCATTGG GGTGGGCTGG   3240
GGTTCAGAGA GGAGGGATTC CCTCCAGGTT ACGTGGCCAA GAAGCAGGGG AGCTGGGTTT   3300
GGGTCAGGCT GGGTGTGGGG TGACCAGCTT ATGCTGTTTG CCCAGGACAG CCTAGTTTTA   3360
GCGCTGAAAC CCTCAGTCCT AGGAAAACAG GGATGGTTGG TCACTGTCTC TGGGTGACTC   3420
TTGATTCCCG GCCAGTTTCT CCACCTGGGG CTGTGTTTCT CGTCCTGCAT CCTTCTCCAG   3480
GCAGGTCCCC AAGCATCGCC CCCTGGCTG TTCCCAAGTT CTTAGGTACC CCACGTGGGT    3540
TTATGAACCA CTTGGTGAGG CTGGTACCCT GCCCCATTC CTGCACCCCA ATTGCCTTAG    3600
TGGCTAGGGG GTTGGGGGCT AGAGTAGGAG GGGCTGGAGC CAGGATTCTT AGGGCTGAAC   3660
AGAGCCGAGC TGGGGGCCTG GGCTCCTGGG TTTGAGAGAG GAGGGCTGG GGCCTGGACT    3720
CCTGGGTCCG AGGAGGAGG GGCTGGGGCC TGGACTCCTG GGTCTGAGGG TGGAGGGACT    3780
GGGGGCCTGG ACTCCTGGGT CCGAGGGAGG AGGGCTGGG GCCTGGACTC GTGGGTCTGA    3840
GGGAGGAGGG GTCGGGGGCC TGGACTTCTG GGTCTTAGGG AGGCGGGCT GGGCCTGGAC    3900
CCCTGGGTCT GAATGGGGAG AGGCTGGGGG CCTGGACTCC TTCATCTGAG GGCGGAAGGG   3960
CTGGGGCCTG GCCTCCTGGG TTGAATGGGG AGGGGTTGGG CCTGGACTCT GGAGTCCCTG   4020
GTGCCCAGGC CTCAGGCATC TTTCACAGGG ATGCCTGTAC                         4060
```

( 2 ) INFORMATION FOR SEQ ID NO:2:

( i ) SEQUENCE CHARACTERISTICS:

( A ) LENGTH: 122 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

| GGTAAGGAGG | ATCGATGGGT | CAGCACAGGC | TGCCAAAGCC | AGGGCCAGTT | AAAGCGACTC | 60 |
| CAATCGAAGA | GAGTAGGTCG | AAGGGAATGT | AGAGCTTCAG | AGTGTCACAC | AGAGTGCTAG | 120 |
| CC | | | | | | 122 |

( 2 ) INFORMATION FOR SEQ ID NO:3:

( i ) SEQUENCE CHARACTERISTICS:
( A ) LENGTH: 120 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

| GGTAAGGAGG | ATCGATGGGT | CAGCACAGGC | TGCCAAAGCC | AGGGCCAGTT | AAAGCCCGGG | 60 |
| CTCGGGCGAC | CTTTGGTCGC | CCGGCCTCAG | TGAGCGAGCG | AGCGCAGAGA | GGGAGTGGCC | 120 |

( 2 ) INFORMATION FOR SEQ ID NO:4:

( i ) SEQUENCE CHARACTERISTICS:
( A ) LENGTH: 122 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:4:

| TTGGCCACTC | CCTCTCTGCG | CGCTCGCTCG | CTCACTGAGG | CCGCCCGGGC | AAAGCCCGGG | 60 |
| CTCGGGCGAC | CTTTGGTCGC | CCGGCCTCAG | TGAGCGAGCG | AGCGCGCAGA | GAGGGAGTGG | 120 |
| CC | | | | | | 122 |

( 2 ) INFORMATION FOR SEQ ID NO:5:

( i ) SEQUENCE CHARACTERISTICS:
( A ) LENGTH: 132 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

| ATCCCTCCCT | CGACTTCCCC | TCTTCCGATG | TTGAGCCCCT | CCAGCCGGTC | CTGGACTTTG | 60 |
| TCTCCTTCCC | TGCCCTGCCC | TCTCCTGAAC | CTGAGCCAGC | TCCCATAGCT | CAGGTCTGGT | 120 |
| CTATCTGCCT | GG | | | | | 132 |

( 2 ) INFORMATION FOR SEQ ID NO:6:

( i ) SEQUENCE CHARACTERISTICS:
( A ) LENGTH: 132 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:6:

TAATACAGGA CCTCCCTAAC ACTCACGTGA CCCTAACCCT ATGACGTAAT TCACGTCACG    60

ACTCCTTCCC TGCCCTGCCC TCTCCTGAAC CTGAGCCAGC TCCCATAGCT CAGGTCTGGT    120

CTATCTGCCT GG    132

( 2 ) INFORMATION FOR SEQ ID NO:7:

( i ) SEQUENCE CHARACTERISTICS:
        ( A ) LENGTH: 132 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

TAATACAGGA CCTCCCTAAC ACTCACGTGA CCCTAACCCT ATGACGTAAT TCACGTCACG    60

ACTCCACCCC TCCAGGAACC CCTAGTGATG GAGTTGGCCA CTCCCTCTCT GCGCGCTCGC    120

TCGCTCACTG AG    132

( 2 ) INFORMATION FOR SEQ ID NO:8:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

ACCAGACCTG AGCTATGGGA GCTGGCTGAG GTTCAGGAGA GGGCAGGGCA GGGAAGGAGA    60

CAAAGTCCAG GACCGGCTGG AGGGCTCAA CATCGGAAGA GGGGAAGTCG AGGGAGGGAT    120

( 2 ) INFORMATION FOR SEQ ID NO:9:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GGGGAGCTGG GTTTGGGTCA GGCTGGGTGT GGGTGACCAG CTTATGCTGT TTGCCCAGGA    60

CAAAGTCCAG GACCGGCTGG AGGGCTCAA CATCGGAAGA GGGGAAGTCG AGGGAGGGAT    120

( 2 ) INFORMATION FOR SEQ ID NO:10:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

GGGGAGCTGG GTTTGGGTCA GGCTGGGTGT GGGTGACCAG CTTATGCTGT TTGCCCAGGA    60

CAGCCTAGTT TTAGCGCTGA AACCCTCAGT CCTAGGAAAA CAGGGATGGT TGGTCACTCT    120

( 2 ) INFORMATION FOR SEQ ID NO:11:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

GGTCCTGGAC TTTGTCCTGG GCA                                           23

( 2 ) INFORMATION FOR SEQ ID NO:12:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

ACGCCCGGGC TTTGGCCGGG CGG                                           23

( 2 ) INFORMATION FOR SEQ ID NO:13:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

AAGCCAGGGC CAGTTAAAGC CCGGGCTC                                28

( 2 ) INFORMATION FOR SEQ ID NO:14:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

CTTTGGCAGC CTGTGCTGA                                                    19

( 2 ) INFORMATION FOR SEQ ID NO:15:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

CTGGACGAGG CGCGTCTGAT G                                               21

( 2 ) INFORMATION FOR SEQ ID NO:16:

( i ) SEQUENCE CHARACTERISTICS:
        ( A ) LENGTH: 21 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:16:

AGCGCAAAGT GACAATGGCC A    21

( 2 ) INFORMATION FOR SEQ ID NO:17:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:17:

GAGAGGTGAC CCGAATCCAC    20

( 2 ) INFORMATION FOR SEQ ID NO:18:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:18:

CACGTGATGT CCTCTGAGCG    20

( 2 ) INFORMATION FOR SEQ ID NO:19:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:19:

GTTGCCAGTC TCGATCCGCC CC    22

( 2 ) INFORMATION FOR SEQ ID NO:20:

( i ) SEQUENCE CHARACTERISTICS:
  ( A ) LENGTH: 19 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:20:

GGGCTGTGGT GAGGAGGGG    19

( 2 ) INFORMATION FOR SEQ ID NO:21:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:21:

AGCGCTAGCT TCCCTGTCCC

20

( 2 ) INFORMATION FOR SEQ ID NO:22:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

ACTGTTCGGG GTATCCCAG

19

( 2 ) INFORMATION FOR SEQ ID NO:23:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

TCCTGCATCC TTCTCCAGGC

20